US012635923B2

(12) United States Patent
Retzkin et al.

(10) Patent No.: US 12,635,923 B2
(45) Date of Patent: May 26, 2026

(54) SYSTEM AND METHOD FOR PATIENT MONITORING

(71) Applicant: EYEFREE ASSISTING COMMUNICATION LTD., Tel-Aviv (IL)

(72) Inventors: Or Retzkin, Tel-Aviv (IL); Itai Kornberg, Ramat Gan (IL)

(73) Assignee: Eyefree Assisting Communication Ltd., Tel-Aviv (IL)

( * ) Notice: Subject to any disclaimer, the term of this patent is extended or adjusted under 35 U.S.C. 154(b) by 0 days.

(21) Appl. No.: 18/809,971

(22) Filed: Aug. 20, 2024

(65) Prior Publication Data

US 2024/0407688 A1     Dec. 12, 2024

Related U.S. Application Data

(63) Continuation of application No. 17/632,368, filed as application No. PCT/IL2020/050858 on Aug. 5, 2020, now Pat. No. 12,097,030.

(51) Int. Cl.
*A61B 5/16*       (2006.01)
*A61B 5/00*       (2006.01)

(52) U.S. Cl.
CPC ............ *A61B 5/165* (2013.01); *A61B 5/0002* (2013.01); *A61B 5/0077* (2013.01); *A61B 5/163* (2017.08);
(Continued)

(58) Field of Classification Search
CPC ........ A61B 5/165; A61B 5/163; A61B 5/0022
See application file for complete search history.

(56) References Cited

U.S. PATENT DOCUMENTS

| | | |
|---|---|---|
| 2004/0193068 A1 | 9/2004 | Burton et al. |
| 2004/0233061 A1 | 11/2004 | Johns |

(Continued)

FOREIGN PATENT DOCUMENTS

| | | |
|---|---|---|
| CN | 1960670 | 5/2007 |
| CN | 106163481 | 11/2016 |

(Continued)

OTHER PUBLICATIONS

"Eye-S: a Full-Screen Input Modality for Pure Eye-based Communication" by M. Porta et al. Association Computing Machinery. 2008 (Year: 2008).*

(Continued)

*Primary Examiner* — Jason M Ip
(74) *Attorney, Agent, or Firm* — Renner, Kenner, Greive, Bobak, Taylor & Weber

(57)       ABSTRACT

The present disclosure provides a system and method for monitoring the cognitive state of a patient based on eye image data. The patient monitoring system including a camera unit configured for recording images of an eye of the patient, and a data processing sub-system in data communication with the camera and being operable to (i) receive and process eye image data from the camera, (ii) classify the eye image data into gestures and identify such gestures indicative of the cognitive state of the patient, and (iii) transmit a signal communicating the cognitive state to a remote unit. The system may further include an actuator module and an output unit wherein the output may be an automated medical questionnaire.

18 Claims, 4 Drawing Sheets

(52) U.S. Cl.
CPC .......... *A61B 5/4809* (2013.01); *A61B 5/6803* (2013.01); *A61B 5/746* (2013.01)

(56)                    References Cited

U.S. PATENT DOCUMENTS

| | | |
|---|---|---|
| 2006/0202841 A1 | 9/2006 | Johns |
| 2006/0203197 A1 | 9/2006 | Marshall |
| 2007/0273611 A1 | 11/2007 | Torch |
| 2009/0058660 A1 | 3/2009 | Torch |
| 2010/0076333 A9 | 3/2010 | Burton et al. |
| 2013/0265231 A1 | 10/2013 | Cleveland et al. |
| 2015/0213634 A1 | 7/2015 | Karmarkar et al. |
| 2016/0354023 A1 | 12/2016 | Falck et al. |
| 2020/0022577 A1 | 1/2020 | Rishoni et al. |
| 2020/0178876 A1 | 6/2020 | Lam |

FOREIGN PATENT DOCUMENTS

| | | |
|---|---|---|
| CN | 109199410 | 1/2019 |
| WO | 2016142933 | 9/2016 |
| WO | 2018098289 | 5/2018 |
| WO | 2019111257 | 6/2019 |

OTHER PUBLICATIONS

"Delirium prevention in critically ill adults through an automated reorientation intervention" by C.L. Munro et al. Heart & Lung. 46 (2017) 234-238 (Year: 2017).*

* cited by examiner

Head unit 202 data processing
subsystem 206

Camera 204

SYSTEM AND METHOD FOR PATIENT MONITORING

TECHNOLOGICAL FIELD

The present disclosure relates to a system that allows the evaluation of a patient's cognitive state based on the patient's eye image data.

BACKGROUND

Lack of communication is a common, unmet need of hospitalized patients, specifically in intensive care units. It is believed that effective communication deprivation could be a contributing factor to the development of intensive care unit (ICU) delirium. Effective communication could be part of prevention and treatment for ICU-delirium in patients. The current standard of communication for the critically ill mechanically ventilated patients, for example, is limited to nodding, writing, and pointing at communication boards.

System and method for enabling user communication by tracking the eye of a user are known.

WO2016142933 discloses such a system with a selection interface that selectively presents a series of communication options to the user. A light sensor detects light reflected from the eye of the user and provides a correlative signal, which is processed to determine a relative eye orientation with respect to the head of the user. Based on the determined relative eye orientation, a selected communication option is determined and implemented.

WO2019111257, which is incorporated herein by reference in its entirety, discloses a control system that interfaces with an individual through tracking the eyes and/or tracking other physiological signals generated by an individual. The system is configured to classify the captured eye images into gestures, that emulate a joystick-like control of the computer. These gestures permit the user to operate, for instance, a computer or a system with menu items.

SUMMARY

A wearable device may serve as a monitoring device, inter alia as an emergency-call device, and to improve patients' orientation in general. In addition, a wearable device could allow broader and more effective communication relative to the current standard of communication for intensive care unit (ICU) patients.

The system of this disclosure is useful for identifying or monitoring a cognitive state of patients that have lost, temporarily or permanently, their ability to communicate in a verbal manner and may be in varying cognitive states. Relevant patient populations for the system of this disclosure are patients whose relevant motor functionalities are impaired. The impairment may be temporary, e.g. in the case of patient in an ICU or patients recovering from trauma (e.g. an accident); or as a result of a permanent morbidity such as paralysis caused by a central or peripheral nervous system disease (e.g. ALS).

The present disclosure concerns a system comprising a camera that captures a sequence of image data of one or both of the patient's eyes. The eye image data is received and processed by a designated data processing sub-system which is operable to classify said eye image data and interpret it into eye gesture, such as eye opening or a blink. The data processing sub-system next identifies, among the resulted eye gestures, unique gestures, gestures patterns, and sequence of gestures that characterize a cognitive state of interest such as awakeness or delirium, based on defined criteria (the criteria may be either fixed or dynamic criteria, for example a criteria which varies across medical disciplines or geographical location, or a criteria derived from a medical textbook). The data processing sub-system may determine that said patient is at, under, or likely to be at or under a cognitive state based on said identification. Upon identification of a cognitive state of interest the sub-system will report the identification to a remote unit by transmitting a signal. For example, for a patient hospitalized in an ICU, who just woke up, as indicated by eyes opening for the first time in days, the system will send an alert signal to any one or a combination of a connected nurse unit, medical staff member, or a family member. The system disclosed herein may also be implemented in any medical or non-medical institution, including but not limited to rehabilitation facilities, nursing facilities, a long-term acute care facilities and senior citizen housing.

By some embodiments the system comprising a wearable headset, wherein the camera is carried on a head unit configured for fitting onto a patient's head.

The system may also provide any output including patient-selected content, medical questionnaire and feedback to the patient, as the system may further comprise an actuator module configured to drive an output unit to present an output to the patient. For example, the system would allow the automated computerized identification of a delirium state in an intensive care patient. Specifically, the system would provide a computerized interface for the well-established Confusion Assessment Method for the ICU (CAM-ICU) test to the patient, who would be able to provide a response via the system (that is via the communication signals the system offers). The system may be configured to receive and process additional physiological data other than eye image data to facilitate the identification of the cognitive state. By some embodiments, the system would also be configured receive and process an additional data such as a verbal input from the user.

The system may, by some embodiments, have a high accuracy rate and brief inference time to allow a simpler yet highly reliable communication system for individuals who's ability to communicate is compromised. This could result in, inter alia, shorter training sessions and a more efficient use of Graphics Processing Unit (GPU) or, by some embodiments faster data transmission to a remote processor (server) which processes and analyzes the transmitted data more efficiently.

According to a first of its aspects, there is provided a patient monitoring system for identifying a cognitive state of a patient, the system comprising a camera configured for recording images of an eye of the patient; a data processing sub-system in data communication with the camera and being operable to (i) receive and process eye image data from said camera; (ii) classify said eye image data into gestures and identifying such gestures indicative of the cognitive state of the patient, and (iii) transmit a signal communicating said cognitive state to a remote unit. The system is developed and designed to monitor a patient. This may include for example any hospitalized patient such as intensive care unit patient, ALS patient, a locked-in patient, a mechanically ventilated patient, a critically ill patient and a patient without an ability to communicate verbally. Additional examples are non-hospitalized patients under medical or caregiver supervision.

The term monitoring encompasses a continuous or intermitted monitoring. By some embodiments said monitoring is seconds or minutes-long, monitoring session for the purpose of medical evaluation. By other embodiments the monitoring is an extended monitoring for example for patients that are hospitalized for days, weeks, months and years.

The term identifying (or its derivations) refers to any binary determination (such as awake or a non-awake, in pain or not, in delirium or not), quantitate determination (for example duration of wakefulness, the amount of a daily wakefulness periods, confusion or pain level at a numeric scale of 1-10, or a likelihood index) or qualitative determination (such as relative sleep quality, disoriented state for instance in relation to yesterday's comparable state) of a cognitive state. The identification may be based on timing, sequence, duration, pattern, or other measures of the patient's eye gestures. The identification encompasses the likelihood, occurrence and duration at any scale (minutes, hours or days) of the cognitive state. The identification may be deduced from the gestures based on pre-defined criteria. The system may also have the options of input by a physician or other caregivers to define definitions or identification rules.

By some embodiment the identification is a predictive identification, encompassing the likelihood of a patient to manifest the cognitive state.

By some embodiment the identification is performed based on a database, gathered based on the patient's own eye gestures or the eye gestures of a group of patients. Said database may be based on historical or real time eye gestures data.

The term cognitive state encompasses wakefulness, sleep state, delirium, cognitive abnormality such as decline, confusion, disorientation, abnormal attention or consciousness, impaired memory, distress, abnormal decision making, frustration, discomfort, pain, and depression. The cognitive state may be the patient natural cognitive state or a cognitive state induced, affected, or modulated by a medical intervention, such as a drug.

By some embodiments the patient monitoring system is screen independent.

By some embodiments the head unit is lightweight head mount, fitted onto the patient's head by a family member, a caregiver or the patient's itself, and may further include a bone conduction speaker\headphone. The head unit may be easily removed. A camera may be carried on said head unit and is configured for recording eye image data that may include images of any one of the eyes, both eyes, any eyelid, or both eyelids of the patient and generating image data representative thereof.

By some embodiments the camera is carried on a head unit configured for fitting onto a patient's head.

By some embodiments, the camera may also be mounted on a frame in the vicinity of the user, e.g. a frame of a bed, a frame that carries medical instruments, etc.

By some embodiments, the camera is fixed relative to the patient's eyes.

By some embodiments, the camera is not fixed relative to the patient's eyes.

By some embodiments, the camera is an infrared camera or a visible light camera.

Typically, operation of the system of this disclosure is independent on the lighting conditions.

By some embodiment the position of the camera (for example as it is attached to the heat unit) is fixed relative to the patients' eye and serves as the only reference point for the captured image data.

By some embodiments, the patient eyes-based communication resembles joystick-like control, rather than detecting the exact location or position the patient is looking at or at a corneal reflection (relative to a screen for example). Also, according to this disclosure there is, typically, no need for any calibration procedure using a screen prior to use, and in fact, there is no need to use screen at all to communicate using the system.

The term joystick-like control as described herein refers to gestures classification comprising tracking the position of the pupil area within an eye image data.

By some embodiments, the joystick-like control is according to the description of WO2019111257, which is incorporated herein by reference in its entirety.

By some embodiments tracking the position of the pupil area is carried out independently of the patients' face.

By some embodiments tracking the position of the pupil area is carried out relative to a fixed camera.

By some embodiments tracking the position of the pupil area is carried out relative to a non-fixed camera.

The pupil area in the context of this disclosure, is the pupil or any portion thereof, identified as indicative of the pupil.

By some embodiments the position of the pupil area is determined based on a databased comprising image data with labeled pupil or eye gestures. Said image data may be acquired from the patient itself or any other patient or group of patients. By some embodiments, the position of the pupil area based on said labeled databased is determined by utilizing machine learning technique, for instance a model considering the likelihood of a given image data to correspond to a particular gesture.

By some embodiments the position of the pupil area may be determined based on its position within a threshold map, wherein a particular position is determined whenever the pupil area touches a border of, or tangent to a border of, the threshold map. For instance, when the pupil area touches the upper border of the threshold map the image data would be classified as an "up" gesture, or when the pupil area is not touching any border of the threshold map the image data would be classified as a "straight" gesture. The threshold map may be derived from a position map, including a region which is within the motion range of the pupil area. By one example, the position map is defined as a rectangle defined by the upper, lower, leftmost and rightmost positions of the pupil area. By some embodiments, the threshold map covers at least one area limited by a border that is at least 20%, 40%, 60%, 80%, 90%, 95% away from the center of the position map. The threshold map is typically at least 80% away from the center of the position map. The position map may be obtained based on the patients' image data or any database comprising image data with or without labeled gestures. Optionally, the position map is within a larger, region of interest (ROI), defined based on anatomical features of the eye or its surrounding.

At times, the position of the pupil area may be determined based on its position within a threshold map comprising more than one key zone. The key zones may be separate, optionally overlapping subregions within the eye image data. At times, a pupil position would be classified as a gesture when the pupil area is so positioned such that it touches a border of, tangent to a border of, or comprised within at least one key zone. The image may be captured at a frame rate of at least 30 Hz, using a camera with a shutter speed of at least $\frac{1}{30}$ sec. By some embodiments, a pupil position will be classified as a gesture if the pupil maintains its gesture-defining position for at least a defined time period, for example 0.05, 0.1, 0.2, 0.3, 0.4, 0.5, 0.6, 0.7, 0.8, 1 or 2 seconds.

By some embodiments, the position of the pupil area is determined by employing computer vision tools, optionally based on circular, curved, and linear features. Optionally, the pupil area identification is carried out based on identifying dark or black pixels in the image data. By some embodiment the center of the pupil is calculated to serves as a reference based on which the eye gestures are classified. By some embodiments the eyes motion range relative to the calculated pupil center is also calculated to optionally serve as a reference for the "middle" eye gesture.

By some embodiments, the position map is a nonconsecutive map or a map comprising more than one area or a zone of an eye image.

By some embodiments the eye gesture is classified based on the image data of a single image data frame. By other embodiments, the eye gesture is classified based on a plurality of image data frames, optionally 2, 5, 10, 20, 50 image data frames. By other embodiments the gesture is classified based on 60%, 70%, 80%, 85%, 90%, 95% or 97% out of the plurality of image data frames within a defined time window or a defined number of image data frames.

By some embodiments the position of the pupil area is determined by employing object detection tools. Optionally the object detection is combined with a deep machine learning model to identify the eye, the pupil and features thereof. Optionally the identified eye features are selected from the eye's iris, outer (limbus) circles or the iris, pupil, inner pupil region, outer pupil region, upper eyelid, lower eyelid, eye corners or any combination thereof.

Optionally, the image data is classified into eye gestures based on any one or combination of the eye features. Said eye features may be selected from eye's iris, pupil, inner pupil region, outer pupil region, outer (limbus) circles or the iris, upper eyelid, lower eyelid, and eye corners.

By some embodiments said eye identification or eye features are derived from the bounding box object detection. The term bounding box may relate to an area defined by two longitudes and two latitudes. Optionally, the latitude is a decimal number in the range of −90 to 90 and the longitude is a decimal number in the range of −180 to 180. By some embodiments the detection is carried out based on labelled data comprising bounding box coordinates and image data labels.

By some embodiments the position of the pupil area is determined by employing machine learning tools or a combination of computer vision and machine learning tools.

Optionally, the combined computer vision and machine learning model is based on a Single Shot Detector (SSD) algorithm.

Optionally, the combined computer vision and machine learning model is based on a You only Look Once (YOLO) algorithm. The YOLO algorithm may include two steps. A first step comprises employing an object detection algorithm to detect at least 2, 3, 4 or 5 key zones within the eye image data. A second step comprises employing a supervised machine learning algorithm to determine the eye pupil within the eye image data, based on the coordinates of said key zones. By some embodiments the position of the pupil area is determined based on a machine learning model. Optionally, said model is based on the patient's image data. Optionally, said model is based on a group of patient's image data. Optionally said model is based on a group of healthy individuals' image data.

Optionally, said model is a supervised, semi-supervised or unsupervised model.

By some embodiments said supervised model is based on manually labeled or automatically labeled image data.

By some embodiments the boundaries between different gestures are defined based on the patients' image data.

By some embodiments, gesture classification is based on employing machine learning techniques. Specifically, the machine learning model may be a neural networks model consisting multiple linear transformations layers and subsequent element-wise nonlinearities. The classification may comprise eye characterization of an individual patient or across patients. By some embodiments the classification estimates the range of eye motion. The machine learning model may employ a classifier selected from: logistic regressions, support vector machine (SVM), or a random forest By some embodiments said model is a deep leaning model, optionally a convolutional neural network (CNN) model. By some embodiments said model classifies image data into at least 5 basic gestures. Optionally said basic gestures are selected from blink, up, down, left, right, middle (straight), diagonal upper left, diagonal upper right, diagonal lower left, and diagonal lower right.

By some embodiments said gesture classification is at an accuracy of at least 80%, 85%, 90%, 95%, 97%, 98, or 99%.

By some embodiments said gesture classification average inference time is up to 100 ms, 125 ms, 150 ms, 175 ms, 200 ms, 240 ms, 250 ms, 260 ms, 270 ms, 300 m, 350 ms, or any number in between. By some embodiments said gesture classification average inference time is in the range of 100-200 ms, e.g. 125±25 ms. Said inference time may correspond to 3-10 frames per second (fps), at times 8 fps.

By some embodiments, a gesture would be classified based on the majority of gestures within a pre-determined time window. A basic time window may be defined (e.g. in the range of 50-200 ms) and the gesture being classified in several consecutive such time windows and then defining as a gesture is when the same classification occurs in the majority of the time windows. For example, in case a 125 ms window is applied, the gesture would be determined every 375 ms (namely after 3 such windows) if the same gesture were classified in 2 out of 3 images. This has the advantage of avoiding hypersensitive response, thus allowing a more stable output.

By some embodiments the machine learning model is further used for headset placement, optionally by classifying whether at least one eye is within the image frame. Optionally the image data is classified into 3 classes, being at least one eye entirely within the frame, no eyes within the frame, and at least one eye centered within the frame.

By some embodiments the machine learning model is first used for headset placements by identifying at least one eye location within the image data. Next, gesture classification is carried out by employing a combination of computer vision and machine learning tools.

By some embodiments a data processing sub-system is a distributed or non-distributed, parallel sub-system.

By some embodiments the classification of said image data into gestures and the identification of such gestures indicative of the cognitive state of the patient is carried out by distributed sub-system components.

By some embodiments a data processing sub-system is in data communication, optionally wireless communication, with the camera and being operable to receive and process image data from said camera, and to further classify said image data into gestures (optionally the classification is carried out according to the joystick-like control described above). Said gestures may comprise voluntary or involuntary eye gesture. Said gestures may comprise straight, center, right, left, up, down, diagonal upper left, diagonal upper right, diagonal lower left, and diagonal lower right positions of the pupil, any sequence of pupil positions, eye closing, eye opening, a curved eye movement, eye movement behind closed eyelid (for example rapid eye movement during sleep), increase or decrease of pupil size (e.g. dilated or constricted pupil), expansion or reduction of part or inner part of the pupil eyelid twitching, blinks and a sequence of eyelid blinks. Said gestures may also include any eye or eyelid movement that is associated with eyelid disorders such as ptosis, eyelid retraction, decreased or increased, blinking and eyelid apraxia.

Optionally, the gestures relate to one of the eyes, or both eyes.

Optionally, the gestures comprise a sequence of 2 or more eyelid blinks.

The gesture may selected from any one or combination of eye gestures known in the art, for example the gesture may be a fixation (stationary gesture or gaze) or a series of fixations and their durations, gestures or gaze points and clusters and distributions thereof.

By some embodiments the system asks the patient to perform a straight gesture in between other gesture.

By some embodiments the blink gesture is identified as a region of dark pixels, or by employing an artificial intelligence model, optionally a machine learning model that classifies the image data of the eye as image of a closed eye (either via supervised or non-supervised leaning).

By some embodiments the eye opening gesture is identified as a region of the pupil, or by employing an artificial intelligence model, optionally a machine learning model that classifies the image data of the eye as image of an open eye or not closed eye.

By some embodiments, the eye closing gesture is identified as a sequence of image data frames of a closed eye after at least one image of not closed eye.

By some embodiments the rapid eye movement (REM) gesture (typical to REM sleep) identified as a sequence of image data frames with rapid changes between them. As a non-limiting example, a sequence of gesture "down-middle-down-middle-down-middle" will serve as an image data classified as a REM gesture.

By some embodiments a gesture would be classified when the pupil area touches a border of, tangent to a border of, or comprises within the threshold map. The image may be captured at a frame rate of at least 30 Hz, using a camera with a shutter speed of at least $\frac{1}{30}$ sec. By some embodiments, a pupil position will be classified as a gesture if the pupil maintains its gesture-defining position for at least a defined time period, for example 0.05, 0.1, 0.2, 0.3, 0.4, 0.5, 0.6, 0.7, 0.8, 1 or 2 seconds.

By some embodiments any one of the type of gestures, number of gestures, the gestures duration, and the corresponding signals and outputs are defined by the patient or a caregiver.

By some embodiments a signal is transmitted based on a single gesture, a plurality of gesture or a sequence of gestures. Optionally a signal is transmitted based on the timing, sequence, duration, pattern, other measures of the patient's eye gestures and any combination thereof.

By some embodiments the eye-opening gesture for at least 1, 3, 5, 7, 10, 30, 60 seconds initiates an "awake" signal.

By some embodiments the eye closing gesture for at least 1, 3, 5, 7, 10, 30, or 60 seconds initiates an "asleep" signal.

By some embodiments a series of 1, 2, 3 or 5 blinks may initiate a "call for help" signal.

By some embodiments, a series of up to 10 blinks, within up to 30 seconds selects a signal.

By some embodiments opening or closing at least one of the eyes for 1, 2, 3, 4, 5, 6, 7, 8, 9, 10, or 30 seconds sends a signal. Optionally, said signal is a rest mode single to the system.

By some embodiments, the signal reports to a caregiver the awakens periods of the patients over a 24 hours period.

By some embodiments, the signal is a recommendation provided by the system regarding the timing of physically visiting the patient' room.

According to another non-limiting embodiments, a patient with a limited ability may operate the system using a single gesture, optionally based on his definitions or eye motion ranges, for instance only a "left" gesture.

By some embodiments the gestures permitting the patient to operate the computer are general viewing at a defined direction (eye gesture), instead of a gesture in which the patient is looking at a particular location (eye gaze). For example, a general left stare may serve as a gesture, even if the patient is not focusing his sight at a specific physical or virtual object.

By some embodiments the identification of gestures indicative of the cognitive state of the patient is carried out based on rules derived from the general medical knowledge and methods known in the art, or based on criteria defined by a nurse, a physician, a caregiver or the patient. Said rules can be either pre-defined or derived after an initial monitoring of an individual patient. Said rules implemented with regards to a patient can be derived from the patient himself or from a typical population group. By some embodiments the identification rule is a fixed rule or rules (based on solid medical knowledge) or dynamic rule (for example based on a single edition of a medical textbook, or a rule that varies across medical disciplines, geographical regions etc.). By some embodiments the rules are dynamic in the sense they are derived based on online artificial intelligence algorithms. Said identification may be carried out as part of monitoring the status of the patient (either during a given time point or in an ongoing manner) or for predicting a cognitive state. said predictive identification, encompassing the likelihood of a patient to manifest the cognitive state.

The cognitive state may be determined in combination with any physiological or non-physiological data. By some embodiments, the cognitive state in determined based on any combination of eye image data and physiological data received by the system. By some embodiments the cognitive state in determined based on any combination eye image data, physiological data, and additional data received by the system. Said additional data may be any quantitative, qualitative, probabilistic, textual, personal or populational data. Said data may be received online or at a pre-defined time point. Said data may originate from the patient, medical staff member, or family member.

Last, once a cognitive state is identified by the system, the data processing sub-system transmit a signal associated with the said cognitive state to a remote unit.

By some embodiments said signal may be any signal, optionally a digitized, computerized signal (for example to put the system into rest mode, or to operate an Internet-of Things (IOT) device), or optionally visual signal (change of light from green to red or vice versa), auditory signal (such as an alert sound), or other digital signals such as a text via text messaging service.

By some embodiments the signal is a word, symbol or sentence, optionally pre-defined by the patient or a caregiver or composed by the patient, optionally using a menu with letters selecting interface.

By some embodiments said remote unit is an alert unit of an intensive care unit, a nurse unit, or a device carried by a caregiver.

By some embodiments the signal to a remote unit is transmitted via wireless communication. The term wireless communication, as used herein may include any form of communication that is independent of an electrical conductor connection, such as Wi-Fi Communication, mobile communication systems, Bluetooth communication, infrared communication, and radio communication. By some embodiments the wireless communication is via a wireless network such as wireless personal area network (WPAN) or a wireless body area network (WBAN).

As a non-limiting example, the signal to a remote unit may corresponds to triggering a device or an equipment in the patient's room, such as turning on or dimming the light in the room, activating a light therapy session, playing media content such as sounds or music, or controlling the room temperature.

As a non-limiting example, the signal to a remote unit may be a signal activating a system for improving or alleviating the patient's medical, emotional, or cognitive state (for example a system for reducing delirium).

By some embodiments the opening of at least one eye image data is being classified as an open eye gesture indicative of a wakeful state, and an alert signal is transmitted to a nurse unit.

By some embodiments the patient monitoring system further comprises an actuator module configured to drive an output unit to present an output to the patient, and wherein the data processing sub-system records reactive image data representative of a reactive eye movement that follows said output, classify said reactive image data into reactive gestures and identifying such gestures indicative of the cognitive state of the patient.

The term output encompasses any sensory output or a content to the patient.

By some embodiments, the output is provided via an Internet-of-Things (IoT) device, such as a smart home device.

By some embodiments, the output is associated with the prevention or reduction a cognitive state, optionally ICU-delirium.

By some embodiments, the output is associated with induction or facilitation of a cognitive state such as a sleep state.

By some embodiments, on top of an automatic actuation described above (from the recording of the image data up to a cognitive state signal transmission), the output may be initiated in response to an eye gesture or a signal. In addition, the output may be selected based on the cognitive state automatically identified by the system, thereby optionally positively affecting the patient cognitive state. For example, a relaxing music, family voices, white noise, or cognitive exercise may be selected in response to the identification of an anxious cognitive state.

By some embodiments the sensory output is visual (for example a message or a question on a screen), auditory (such as a vocal instruction or a question), a tactile output (such as a touch stimulus across the patients' foot) or any combination thereof.

By some embodiments the term content is any content either generic, or personally generated content. These may include a generic medical information video, or a message delivered to the patient by his physician, nurse or caregiver.

By some embodiments the content is any media content selected by the patient.

By some embodiments the media content is selected in order to better the patients' functional performance or a medical indication such as to lower stress.

By some embodiments the media content is any visual or auditory content familiar to the patient such as voices of family members or known environment. The auditory content may be a pre-recorded media file or transmitted online. By one embodiment, the content is a menu system that permits the patient to navigate through a menu that is presented to the patient and controlled through his eye gestures by selecting menu items using eye gestures. The presentation of the menu may be an audible presentation (by means of a loudspeaker, earphones, headphones, implanted audible device, etc.) or a visual presentation (through a display on a screen, a small display in front the patient, etc.). The menu may be hierarchical, meaning that a selection of a menu item may open other, lower hierarchy selectable options.

By some embodiments, the menu is according to the description of WO2019111257, which is incorporated herein by reference in its entirety.

By some embodiments the output is a human, digital or automatic medical questionnaire. At times, the type and content of the medical questionnaire is determined based on the patients' response to a previous question. At times, the type of medical questionnaire, and the questions of said medical questionnaire are determined based on reactive gestures. By one embodiment said medical questionnaire is Confusion Assessment Method for the ICU (CAM-ICU). By one embodiment the opening of at least one eye gesture initiates the CAM-ICU output.

By some embodiments the output is a visual or audio indicating to the patient the day, time and location of the patient.

By some embodiments the output instructs the user how to respond (optionally to said medical questionnaire) using his eye gestures.

The term reactive image data, refers to image data recorded in response to an output provided to the patient.

The term reactive eye movement refers to eye movement recorded in response to an output provided to the patient.

The term reactive eye gesture refers to eye gesture classified based on a reactive eye movement or reactive image data. In some embodiments the reactive gestures are indicative of the cognitive state of the patient.

By one embodiment the opening of at least one eye gesture initiate the CAM-ICU output, and the reactive eye gestures are indicative of a delirium state. As a non-liming example, the system will execute the CAM-ICU test by outputting multiple-choice questions and the patient will communicate his answers by blinking.

As another non-liming example, the system will execute a reorientation evaluation by outputting the current time, date and location and the patient will respond by maintaining open eyes gesture for a defined time interval.

Also, as another exemplary and non-limiting embodiment, the patient may be prompted by audio or visual output to select between several options, e.g. "UP" (namely upwards gesture) for one selection, "DOWN" for another, etc. By further exemplary and non-limiting embodiment, the patient may be presented (e.g. through an audio output) with options and thereby prompting the patient to perform a gesture in a specific or non-specific direction, make a series of blinks, close the eyelids for a defined period, etc., when the specific choice is presented. The latter is useful, for example, for a quick selection of letters for writing texts. This embodiment may also serve the patient in responding the medical questionnaire.

Yet according to another exemplary and non-limiting embodiment, said medical questionnaire is a pain scale, optionally selected from a Numeric Rating Scale, Stanford Pain Scale, Brief Pain Inventory, Wong-Baker Faces, Global Pain Scale, Visual Analog Scale, and McGill Pain Index. An additional medical questionnaire according to the present disclosure is an air hunger or a breathing discomfort questionnaire.

In some embodiments the data processing sub-system is further operable to receiving and classifying one or more physiological parameters, and identifying such said physiological parameters, or any combination or said gestures and physiological parameters, indicative of the cognitive state of the patient.

By some embodiments the identification involved the likelihood of the patient to manifest a cognitive state based on a combination of said eye gestures and physiological parameters. By some embodiments said combination is rapid eye movements with elevated heart rate.

By other embodiment, the cognitive state is identified based on a series of gestures accumulated over a time period at a scale of minutes, hours, days, or months.

The scale minutes encompasses up to 10, 20, 30, 60, 120, or 240 minutes.

The scale of days encompasses up to 1, 2, 3, 4, 5, 7, 14, 30, or 60 days.

The scale of months encompasses 1, 2, 4, 6, 8, 12, or 24 months.

At time the cognitive state is assessed based on the spontaneous or ongoing gestures performed by the patients, independent of an input provided by the system.

The term physiological parameters encompass any sample of a physiological measurement that is any signal that may be acquired from the patients' body, including any signal acquired from the patients' neural, cardiac, somatosensory, vocal, and respiratory system as well as motion of selected muscles. The physiological parameters may be recorded by any sensor utility or a measuring device, a microphone, spirometer, galvanic skin response (GSR) device, touch or pressure probes, electrodermal response probe (skin conductance probe), electroencephalography (EEG) device, electroencephalography (ECoG) device, electromyography (EMG), electrooculography (EOG), and electrocardiogram.

By some embodiments the physiological parameters, or any combination of said eye gesture and physiological parameters are indicative of a cognitive state of a patient.

By some embodiments there is provided a patient monitoring system comprising a plurality of patient monitoring systems (or sub-systems). By some embodiments, each of said plurality of patient monitoring systems monitors a different patient.

By some embodiments said system further comprising a centralized processor being operable for receiving signals representative of said cognitive states from each of said patient monitoring systems (or sub-systems) and classifying such signals according to one or more defined criteria. By some embodiments the classification, carried out by the centralized processor, is based on criteria defined by a physician or caregiver. Said criteria may represent medical urgency considerations, temporal considerations, spatial consideration and any combination thereof.

According to a non-limiting example, a set of patients hospitalized at the same department are being monitored by said plurality of patient monitoring systems (or sub-systems, wherein each patient in being monitored by a sub-system), and the signals transmitted by said systems are being classified by the centralized processor so that the nurse unit is receiving the alerts ranked based on their medical urgency.

By some embodiments, the signal in an integrated signal, reporting an awake state of at least 2, 4, 6, 8, 10, 20, 50, 100 patients.

By some embodiments, the signal in an integrated signal, reporting a sleep state of at least 2, 4, 6, 8, 10, 20, 50, 100 patients.

The system according to some embodiments of the present disclosure involves a training period, measured as the time needed to a patient to execute at least one signal using the device, of up to 5, 10, 20, 30, 60, 120, and 360 minutes, optionally measured from the first time point of setting up the system with respect to the patient, for example proper mounting of the headset.

In some embodiments the data processing sub-system is further operable to receiving and classifying any additional data (physiological or non-physiological). A non-limiting example is receiving and classifying patients' answers (e.g. via reactive eye gestures or otherwise) to a medical questionnaire (optionally said medical questionnaire is output by the system), to obtain an accumulated result of a medical questionnaire. As an example the patient may response to a stress level questionnaire via the system, and the results of said questionnaire would be received and classified by the system, optionally in combined with any one or combination of the eye image data, physiological data and additional data. Said additional data may be any one or combination of populational data (such as epidemiological data), personal data (genetic predisposition), medical history data or a non-medical data such as socioeconomical background. Said additional data may be transmitted to the data processing sub-system directly or, as a non-limiting example, via a nurse unit. In some embodiments the data processing sub-system is further operable to receiving and classifying additional data and identifying any additional data or combination of said gestures with additional data, indicative of the cognitive state of the patient.

By some embodiments the additional data, or any combination of said eye gesture, physiological parameters and additional data are indicative of a cognitive state of a patient.

In some embodiments the data processing sub-system receives and processes (for example by means of natural language processing) audio data. For example, once the patient is asked a question by another person, e.g. a caregiver, the data processing sub-system may receive and process the physician speech and propose to the patient a response based on a contextual analysis of the speech of the other person and the language of the patient, including instructions to the patient, in his own language. This embodiment would allow a patient in a foreign country to easily communicate with the local physical and caregiver.

According to a second of its aspects there is provided a method for identifying a cognitive state of a patient, the method comprising (a) recording image data of at least one of patient's eyes;

(b) classifying said image data into gestures; (c) identifying such gestures indicative of the cognitive state of the patient; and (d) transmitting a signal communicating said cognitive state to a remote unit.

By some embodiments, the method further comprising proving an output to the patient.

By some embodiments, the method further comprising (a) recording reactive image data representative of a reactive eye movement that follows said output; (b) classifying said reactive image data into reactive gestures; and (c) identifying such gestures indicative of the cognitive state of the patient.

By some embodiments, the method further comprising (a) receiving and classifying one or more physiological parameters; and (b) identifying such said gestures and physiological parameters, or any combination thereof, indicative of the cognitive state of the patient.

By some embodiments there is provided a method for identifying a cognitive state of a patient, the method comprising (a) recording eye images of a patient from a plurality of patient monitoring systems; (b) classifying said image data into gestures; (c) identifying such gestures indicative of the cognitive state of the patient to obtain an identified cognitive state; (d) classifying said identified cognitive state according to one or more defined criteria.

By some embodiments there is provided a method for an integrated patient monitoring for identifying a cognitive state of a plurality of patients, the method comprising (a) recording eye images of each patient from a plurality of patient monitoring systems; (b) classifying said image data from each of said systems into gestures; (c) identifying such gestures indicative of the cognitive state of each patient to obtain an identified cognitive states; (d) classifying said identified cognitive states according to one or more defined criteria and (e) transmitting an integrated signal communicating said cognitive states to a remote unit.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1:
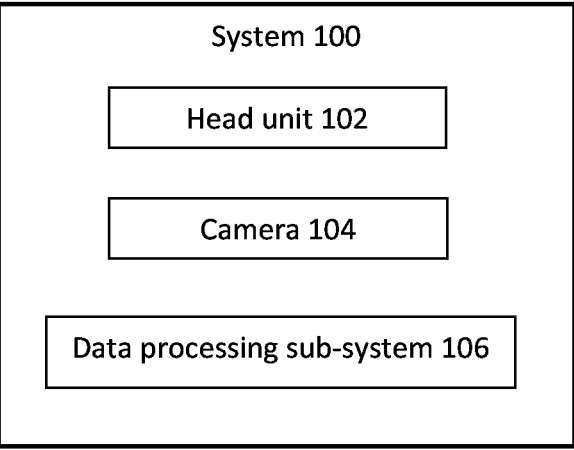
FIG. 1 is a schematic block diagrams of a system in accordance a non-limiting embodiment of this disclosure.

Reference is first made to FIG. 1 illustrating a schematic block diagram of a patient monitoring system in accordance with a non-limiting embodiment of this disclosure. The patient monitoring system 100 comprises a camera 104, mounted on a head unit 102 configured for fitting onto a patient's head. The camera may also be mounted on any fixed frame in the vicinity of the patient. The camera 104 is operable for continuously capturing images of one or both of the patient's eye and eyelid and generating image data representative thereof. The system 100 includes a parallel or distributed data processing sub-system 106 that is in data communication with the camera 104. The data processing sub-system 106 receive and process eye image data from said camera, classify said eye image data into gestures and identify such gestures indicative of the cognitive state of the patient. Next the data processing sub-system 106 transmit a signal communicating said cognitive state to a remote unit.

As a non-limiting example, an ICU patient hospitalized unconscious for several days, is being monitored by the patient monitoring system 100. A caregiver had placed the wearable head unit 102 onto the patient's head. Once the patient opens his eyes for the first time, his eyes movement is captured by the camera 104. The image data from said camera 104 is received by the data processing sub-system 106. Next the image data is classified into gestures, and in case an eye-opening gesture is classified, a wakeful state is indicated and a "call for help" signal is transmitted wirelessly to the nearest nurse unit.

Figure 2:
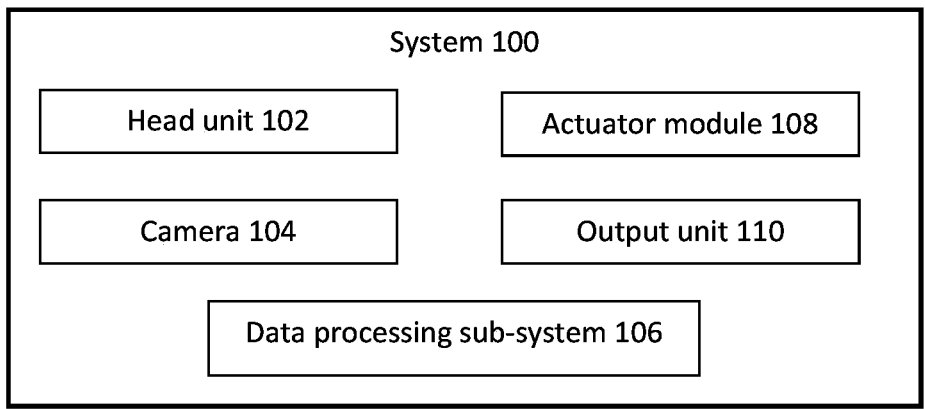
FIG. 2 is a schematic block diagram of a system in accordance with another non-limiting embodiment of this disclosure.

FIG. 2 shows a block diagram of the system of the present disclosure, wherein the system further includes an actuator module 108 that drives the first output unit 110. Output unit 110 may be a visual display, e.g. digital screen, or an audible device, e.g. speaker, headphones, etc.

As a non-limiting example, a patient hospitalized and suspected to suffer from delirium is wearing the head unit 102 and is being monitored by the patient monitoring system 100. Once the patients blink twice, his eyes movement is captured by camera 104 and classified as a sequence of two blinks gesture by the data processing sub-system 106. The said gesture initiates an output of a digital CAM-ICU medical questionnaire via the output unit 110 that is driven by the actuator module 108. The patients respond to the CAM-ICU evaluation by performing a reactive eye movement, captured by the camera 104, and classified into reactive eye gestures via the data processing sub-system 106. These reactive eye gestures are taken to indicate whether the patient is indeed in a delirium state. If indeed a delirium state is identified by the data processing sub-system 106 a delirium signal is transmitted to the patient's physician by said data processing sub-system 106.

Figure 3:
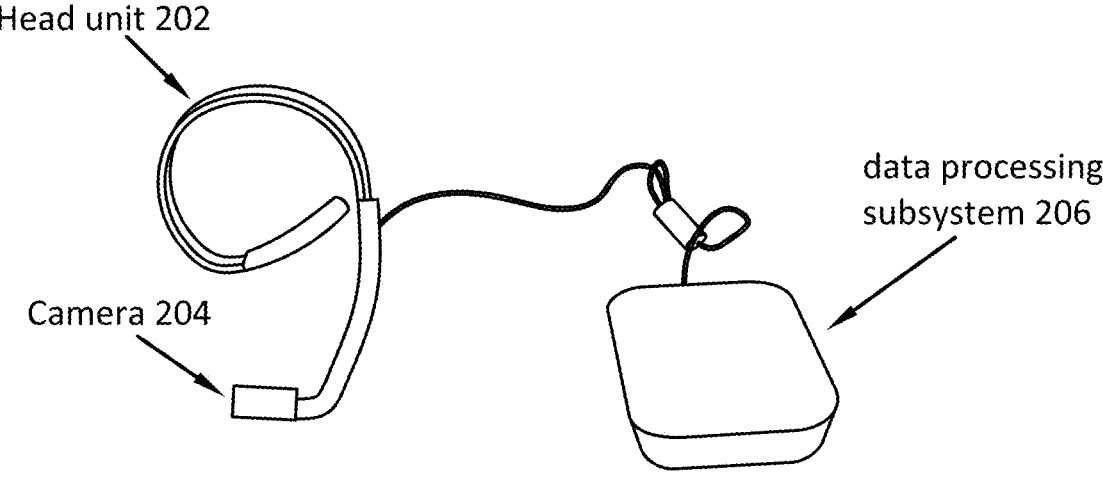
FIG. 3 displays an exemplary embodiment of the system.
Figure 4:
FIG. 4 displays an exemplary embodiment of the system as may be worn by a patient.

FIG. 3 and FIG. 4 show a non-limiting exemplary element of the system of this disclosure. The elements in FIG. 3 and FIG. 4 are assigned with numerical indices that are shifted by 100 from the indices of the elements shown by FIG. 1. For example, head unit indicted 102 in FIG. 1 is indicated by 202 in FIG. 3. Accordingly, the reader may refer to the above text for details regarding the functionally of these elements.

FIG. 3 shows a non-limiting example of the system, including a head unit 202, a camera 204 and a non-distributed data processing sub-system 206, which is in wireless communication (e.g. Wi-Fi, Bluetooth) with a remote unit.

FIG. 4 shows a non-limiting illustration of the system as may be worn by a potential patient.

Figure 5:
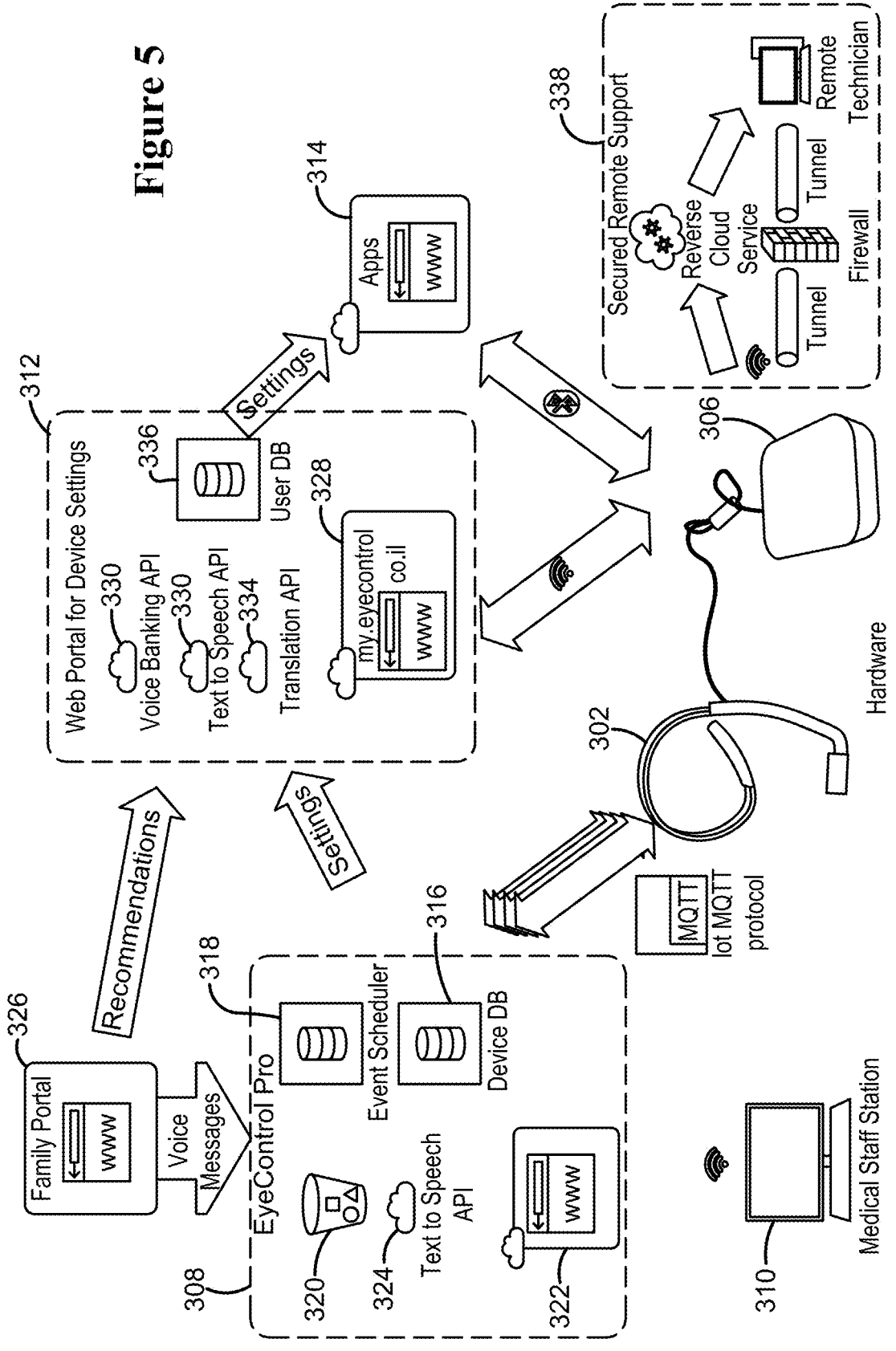
FIG. 5 shows an exemplary embodiment of a high-level system architecture.

FIG. 5 shows a high-level system architecture according to a non-limiting exemplary embodiment. According the exemplary system, the system comprises a data processing sub-system 306 and a headset 302. The system is in remote bi-directional communication with (i) a medical staff server 308 (for example via IoT protocol) which communicates with a remote medical staff station 310 (ii) a device settings cloud server 312, via wi-fi communication and (iii) web-based additional applications 314 via Bluetooth communication. The medical staff server comprises a system database 316, an event scheduler 318 (for example for allowing the medical staff to schedule a calendar event for a specific patient such as a "good morning" greeting every day at 08:00 or an initiation of the CAM-ICU or other medical questionnaire every 12 hours), a server 320 for storing and retrieving data (such as the media files for the vocal menu, a World Wide Web (WWW) page 322, and a text-to-speech application programming interface (API) 324. The staff server receives data via a remote family portal 326, for example voice messages. The family portal 326 may transmit recommendations to the device setting cloud server which comprise a web portal 328. The device settings cloud server comprises a voice banking 330 (generate an original content using synthetic voice based on a previously recorded voice), text-to-speech 332, and translation 334 APIs as well as a user database 336.

The system comprises an output unit and an actuator module for driving an output selected from questionnaires, sets of audible questions and answers, orientation messages (location, date, time), music, recordings of family members etc. The outputs may be triggered by eye gestures classified by the system. In addition, response to said outputs may be provided by the patient via a reactive gesture classified by the data processing sub-system. A response may include answering questions. Overall, the system allows more natural, relaxed and controlled environment for the patient, thereby improving the quality of the hospitalization and reducing negative emotions during hospitalization such as feeling lack of control, anxiety, fear of not being able to communicate and more. The system is also linked to a secured remote support cloud 338 enabling a reverse tunnel to a remote technician service.

Figure 6:
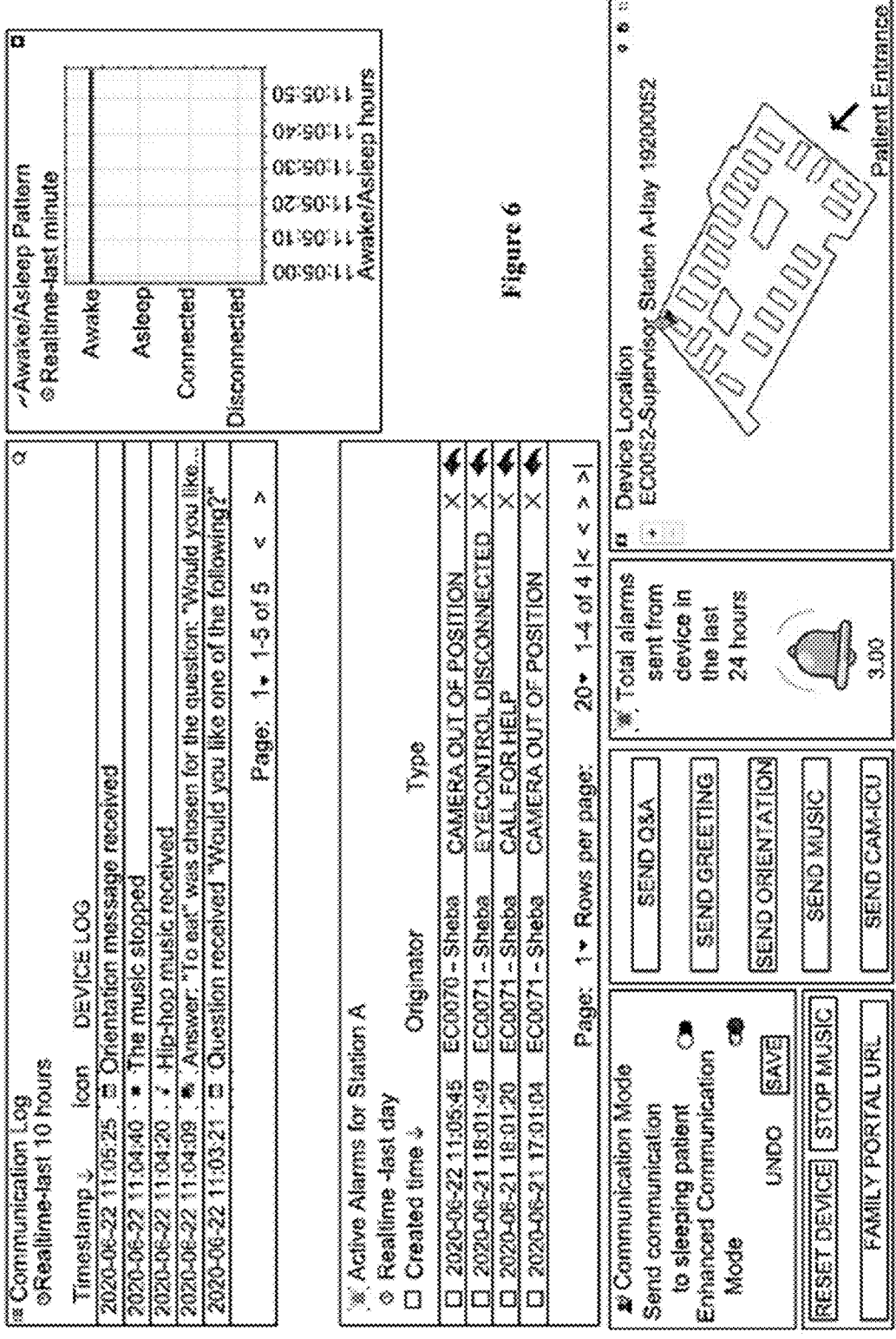
FIG. 6 shows an exemplary embodiment of a display screen, or dashboard, of a remote unit being a medical staff station

FIG. 6 shows an example of a possible screen display (a dashboard) in a medical staff station which shows:

Communication log including answers of the patient to questions sent from station in the form of audio (via speech).

Communication module presenting communication options to the medical staff

Sleeping/awake pattern of the patient

Log of total alerts and alerts which require physical intervention by the staff in the user room (user call for help alert, camera is dislocated, device is disconnected from network etc.)

Device location within the medical department reminder

Activity log of the user and device

Medical assessment questionnaire results (such as CAM-ICU, pain scale and more)

Music, orientation, and family voice recordings buttons

The invention claimed is:

1. A patient monitoring system for identifying a cognitive state of a patient, the system comprising a camera unit configured for recording images of an eye of the patient;

a data processing sub-system in data communication with the camera and being operable to i. receive and process eye image data from said camera;

ii. classify said eye image data into gestures and identify such gestures that are indicative of the cognitive state of the patient to thereby predict a cognitive state of the patient, and iii. transmit a signal communicating said cognitive state to a remote unit;

a processing circuitry; and an output unit;

wherein said processing circuitry is configured to operate said output unit to present an output to the patient;

wherein said output comprises media content that comprises any visual or auditory content, the media content being selected based on the predicted cognitive state by the system to thereby positively affect the patient's cognitive state;

wherein said output further comprises one or more questions and instructions to the patient on how to respond to the one or more questions by using eye gestures, and the one or more questions are output following said output of media content, wherein the instructions specify how to use eye gestures to indicate specific responses to each question; and wherein said data processing sub-system records reactive image data representative of a reactive eye movement that follows said output, classify said reactive image data into reactive gestures and identifying such gestures being indicative of the cognitive state of the patient to determine an updated cognitive state of the subject following said output.

2. The patient monitoring system of claim 1, wherein the camera is carried on a head unit configured for fitting onto a patient's head.

3. The patient monitoring system of claim 1, wherein the cognitive state is selected from wakefulness, delirium, cognitive decline, confusion, disorientation, abnormal attention, consciousness, pain, and depression.

4. The patient monitoring system of claim 1, wherein the remote unit is an alert unit of an intensive care unit, a nurse unit, or a device carried by a caregiver.

5. The patient monitoring system of claim 1, wherein the gesture is selected from opening of at least one eye, closing at least one eye, pupil position, sequence of pupil positions, and sequences of eyelid blinks.

6. The patient monitoring system of claim 1, wherein the opening of at least one eye gesture is indicative of a wakeful state, and wherein an alert signal is transmitted to a nurse unit.

7. The patient monitoring system of claim 1, wherein the signal to the remote unit is transmitted via wireless communication.

8. The patient monitoring system of claim 7 wherein said output is an automatic medical questionnaire.

9. The patient monitoring system of claim 8, wherein said medical questionnaire is selected from any one of Confusion Assessment Method for the ICU (CAM-ICU), pain scale and air hunger or breathing discomfort questionnaire.

10. The patient monitoring system of claim 1, wherein the data processing sub-system is further operable to receiving and classifying one or more physiological parameters, and identifying such said physiological parameters, or any combination of said gestures and physiological parameters, indicative of the cognitive state of the patient.

11. A patient monitoring system comprising a plurality of patient monitoring systems of claim 1.

12. The patient monitoring system of claim 11, further comprising a centralized processor being operable for receiving signals representative of said cognitive states from each of said patient monitoring systems and classifying such signals according to one or more defined criteria.

13. A patient monitoring method for identifying a cognitive state of a patient, the method comprising a. recording image data of at least one of patient's eyes;

b. classifying said image data into gestures;

c. identifying such gestures that are indicative of the cognitive state of the patient; transmitting a signal communicating said cognitive state to a remote unit;

d. providing an output to the patient that comprises media content that comprises any visual or auditory content, the media content being selected based on the predicted cognitive state by the system to thereby positively affect the patient's cognitive state, wherein said output further comprises one or more questions and instructions to the patient how to respond to the one or more questions by using eye gestures, and the one or more questions are output following said output of media content, wherein the instructions specify how to use eye gestures to indicate specific responses to each question;

e. recording reactive image data representative of a reactive eye movement that follows said output;

f. classifying said reactive image data into reactive gestures; and g. identifying such gestures indicative of the cognitive state of the patient to determine an updated cognitive state of the subject following said output.

14. The patient monitoring method of claim 13, wherein said output is an automatic medical questionnaire.

15. The patient monitoring method of claim 14, wherein said medical questionnaire is selected from any one of Confusion Assessment Method for the ICU (CAM-ICU), pain scale and air hunger or breathing discomfort questionnaire.

16. The patient monitoring method of claim 13, further comprising a receiving and classifying one or more physiological parameters; and identifying such of said gestures and physiological parameters, or any combination thereof, indicative of the cognitive state of the patient.

17. A patient monitoring system for identifying a cognitive state of a patient, the system comprising:

a camera unit configured for recording images of an eye of the patient;

a data processing sub-system in data communication with the camera and being operable to:

i. receive and process eye image data from said camera;

ii. classify said eye image data into gestures and identify such gestures that are indicative of the cognitive state of the patient to thereby predict a cognitive state of the patient, and iii. transmit a signal communicating said cognitive state to a remote unit;

a processing circuitry; and an output unit;

wherein said processing circuitry is configured to operate said output unit to present an output to the patient;

wherein said output comprises media content that comprises auditory content, the media content being selected based on the predicted cognitive state by the system to thereby positively affect the patient's cognitive state;

wherein the media content comprises voices of family members;

wherein said output further comprises one or more questions and instructions to the patient on how to respond to the one or more questions by using eye gestures, and the one or more questions are output following said output of media content, wherein the instructions specify how to use eye gestures to indicate specific responses to each question; and wherein said data processing sub-system records reactive image data representative of a reactive eye movement that follows said output, classify said reactive image data into reactive gestures and identifying such gestures being indicative of the cognitive state of the patient to determine an updated cognitive state of the subject following said output;

wherein the cognitive state is selected from wakefulness, delirium, cognitive decline, confusion, disorientation, abnormal attention, consciousness.

18. The patient monitoring system of claim 1, wherein the cognitive state is delirium.

* * * * *